United States Patent
Diamond et al.

(10) Patent No.: US 7,837,631 B2
(45) Date of Patent: Nov. 23, 2010

(54) BIOPSY FORCEPS WITH REMOVABLE JAW SEGMENTS

(75) Inventors: Bruce H. Diamond, Wellesley, MA (US); Rodney C. Tullett, Seattle, WA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 10/389,851

(22) Filed: Mar. 14, 2003

(65) Prior Publication Data

US 2004/0181169 A1    Sep. 16, 2004

(51) Int. Cl.
   *A61B 10/00*    (2006.01)
   *A61B 17/00*    (2006.01)
(52) U.S. Cl. .................. 600/564; 606/205; 606/206
(58) Field of Classification Search .............. 600/562, 600/564, 567; 606/205–208, 167, 170, 174
See application file for complete search history.

(56) References Cited

U.S. PATENT DOCUMENTS

| | | | |
|---|---|---|---|
| 5,052,402 A | 10/1991 | Bencini et al. | |
| 5,109,867 A * | 5/1992 | Twyford, Jr. | 600/585 |
| 5,133,735 A | 7/1992 | Slater et al. | |
| 5,171,258 A | 12/1992 | Bales et al. | |
| 5,222,961 A * | 6/1993 | Nakao et al. | 606/143 |
| 5,238,002 A * | 8/1993 | Devlin et al. | 600/564 |
| 5,295,952 A * | 3/1994 | Pietrafitta | 604/1 |
| 5,454,378 A | 10/1995 | Palmer et al. | |
| 5,486,185 A * | 1/1996 | Freitas et al. | 606/142 |
| 5,499,997 A * | 3/1996 | Sharpe et al. | 606/206 |
| 5,618,304 A | 4/1997 | Hart et al. | 606/205 |
| 5,676,678 A * | 10/1997 | Schad | 606/170 |
| 5,743,905 A * | 4/1998 | Eder et al. | 606/32 |
| 5,779,686 A | 7/1998 | Sato et al. | |
| 5,855,590 A * | 1/1999 | Malecki et al. | 606/205 |
| 5,871,453 A * | 2/1999 | Banik et al. | 600/564 |
| 5,928,255 A * | 7/1999 | Meade et al. | 606/170 |
| 5,964,717 A | 10/1999 | Gottlieb et al. | |
| 5,984,938 A * | 11/1999 | Yoon | 606/170 |
| 6,074,408 A | 6/2000 | Freeman | |

(Continued)

FOREIGN PATENT DOCUMENTS

JP    5-91974    4/1993

(Continued)

OTHER PUBLICATIONS

An English language version of a communication from the Japanese Patent Office citing the above Japanese Patents in Patent Application No. 2006-508859, mailed Aug. 12, 2009.

*Primary Examiner*—Max Hindenburg
*Assistant Examiner*—Jonathan M Foreman
(74) *Attorney, Agent, or Firm*—Finnegan, Henderson, Farabow, Garrett, & Dunner, LLP

(57) ABSTRACT

A biopsy forceps (10) has a handle (20), a bite device (15), and a pair of tissue cutting jaws (18) that are separated by an elongate sheath (12). The tissue cutting jaws (18) may be opened and closed to obtain a tissue sample. The bite device (15) with tissue cutting jaws (18) is removable from the distal end of the forceps (10) so that a physician can use a different pair of tissue cutting jaws (18) for each sample obtained.

11 Claims, 3 Drawing Sheets

U.S. PATENT DOCUMENTS

| | | | |
|---|---|---|---|
| 6,193,671 B1 * | 2/2001 | Turturro et al. | 600/564 |
| 6,423,060 B1 * | 7/2002 | Ouchi | 606/41 |
| 6,551,316 B1 * | 4/2003 | Rinner et al. | 606/57 |
| 2001/0007925 A1 * | 7/2001 | Ritchart et al. | 600/567 |
| 2003/0176766 A1 * | 9/2003 | Long et al. | 600/106 |
| 2004/0092978 A1 * | 5/2004 | Surti | 606/157 |

FOREIGN PATENT DOCUMENTS

| | | |
|---|---|---|
| JP | 9-508560 | 9/1997 |
| JP | 10-510169 | 10/1998 |
| WO | WO 96/10957 | 4/1996 |
| WO | WO 96/19150 | 6/1996 |

* cited by examiner

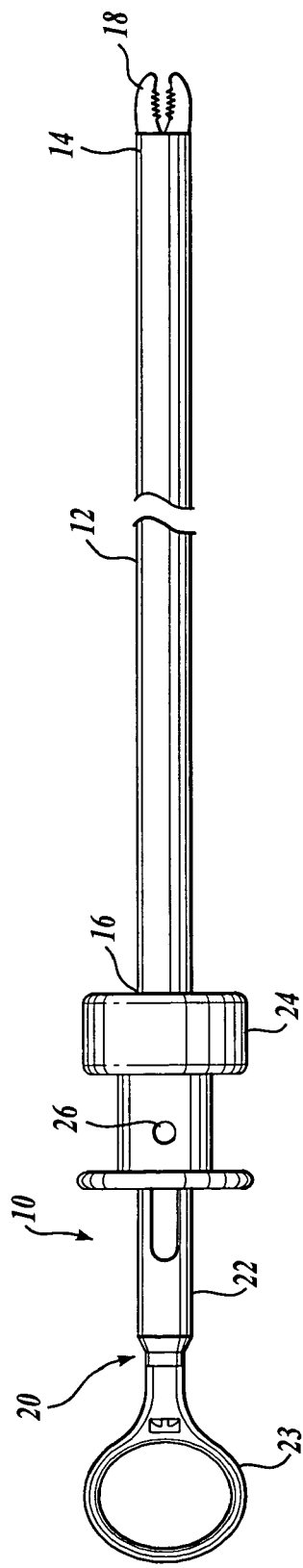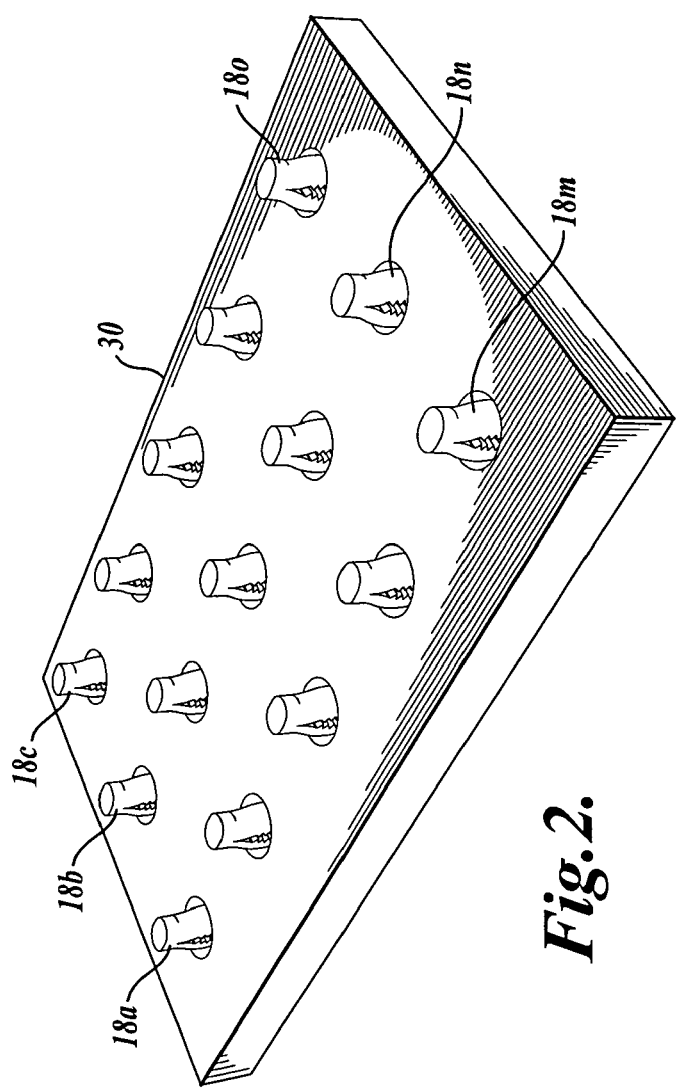
Fig.1.
Fig.2.

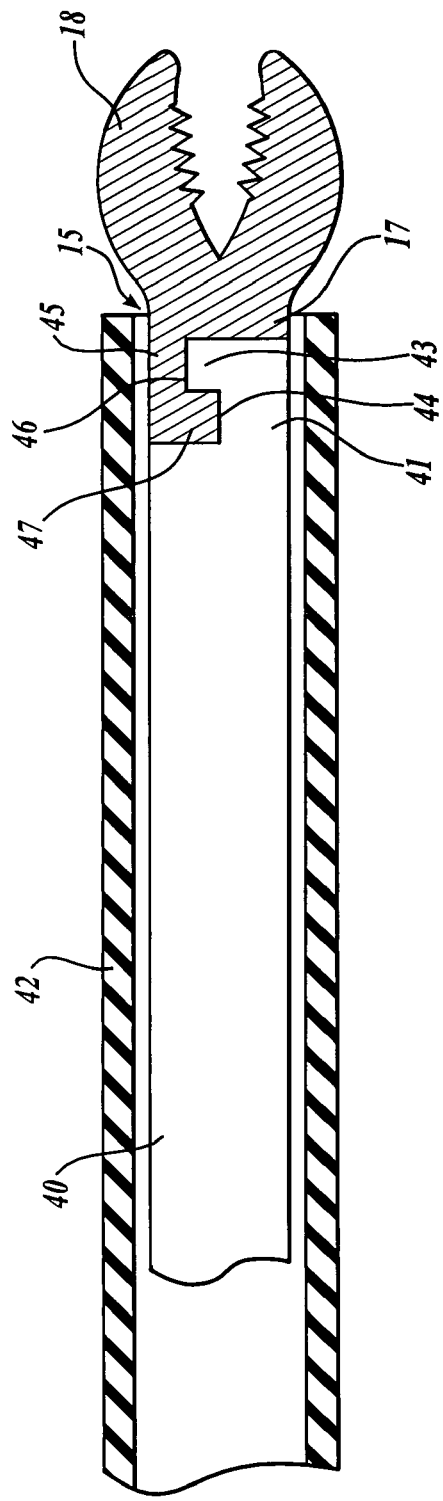
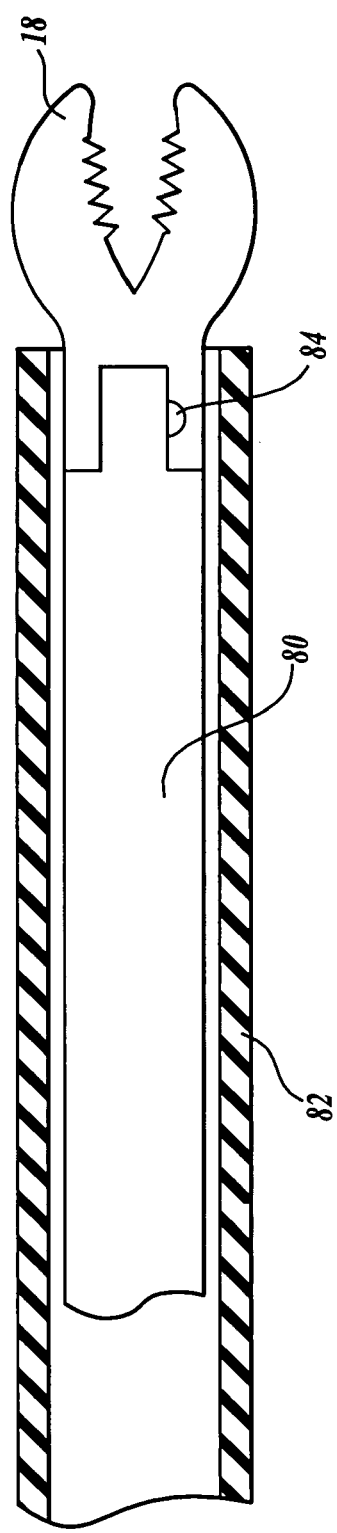

BIOPSY FORCEPS WITH REMOVABLE JAW SEGMENTS

FIELD OF THE INVENTION

The present invention relates to medical devices in general, and to biopsy forceps in particular.

BACKGROUND OF THE INVENTION

A common medical device used with endoscopic procedures is a biopsy forceps. Such a device is an elongate cutter having a handle and a pair of tissue cutting jaws that are separated by a catheter or sheath. The tissue cutting jaws are operated by a cable or other mechanism that extends through the sheath into the handle. A physician inserts the forceps into a working channel of an endoscope and activates the jaws to obtain a tissue sample for analysis by a pathologist.

In the past, if a physician wanted to biopsy more than one area of tissue, the physician would insert the device into the endoscope, obtain a biopsy sample and retract the device from the endoscope in order to place the tissue sample in an appropriate container. Alternatively, some biopsy forceps are multiple bite devices that can hold more than one tissue sample. The problem with each type of forceps design is that cross-contamination may occur between different tissue samples thereby providing the physician with an inaccurate assessment of the diseased state of the patient. While it is possible that the physician could use separate biopsy forceps for each sample, such a solution would require either many disposable devices to be used or could generate many devices that must be sterilized.

Therefore, there is a need for a biopsy forceps that can obtain multiple tissue samples with less likelihood of cross-contamination and that does not require different devices to be used for each tissue sample.

SUMMARY OF THE INVENTION

To solve these and other problems, the present invention is a biopsy forceps having a removable bite device with cutting jaws. The biopsy forceps has a handle and a bite device with a pair of cutting jaws, separated by a catheter or sheath. A physician manipulates the handle to actuate the cutting jaws to retrieve a tissue sample. The bite device with cutting jaws can be selectively removed after each tissue sample is obtained and a new bite device with a new pair of jaws attached in order to obtain another tissue sample. Sets of cutting jaws can be distributed in a tray or other carrying device that allows the physician to easily attach a new pair of cutting jaws after each tissue sample is obtained.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 illustrates a biopsy forceps in accordance with one embodiment of the present invention;

FIG. 2 illustrates a tray of removable bite devices with tissue cutting jaws in accordance with an aspect of the present invention;

FIG. 3 illustrates one embodiment of a mechanism for removably securing a bite device with a pair of tissue cutting jaws to the distal end of the biopsy forceps;

FIG. 5 illustrates yet another embodiment of a mechanism for removably securing a bite device with a pair of tissue cutting jaws to the distal end of a biopsy forceps.

DETAILED DESCRIPTION OF THE PREFERRED EMBODIMENT

Figure 4:
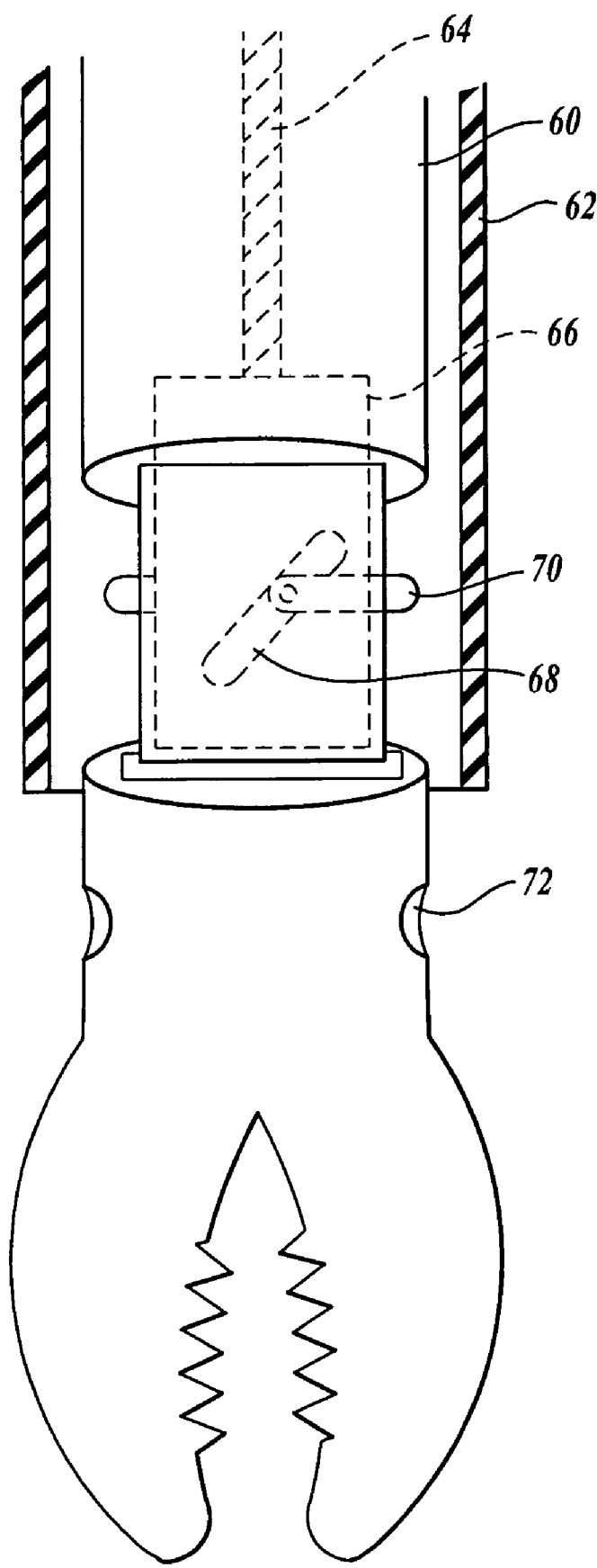
FIG. 4 illustrates yet another embodiment of a mechanism for removably securing a bite device with a pair of tissue cutting jaws to the distal end of a biopsy forceps.

As shown in FIG. 1, a biopsy forceps 10 in accordance with one embodiment of the present invention includes a catheter or sheath 12 having a distal end 14 and a proximal end 16. At the distal end 14 of the sheath 12 is a pair of tissue cutting jaws 18. The tissue cutting laws 18 include a plurality of teeth. The tissue cutting jaws 18 are removably secured to the biopsy forceps such that the jaws 18 can be exchanged for another pair of jaws after a tissue sample is obtained. A handle 20 at the proximal end of the sheath includes a stationary portion 22 having a thumb ring 23 and a slide 24 that moves with respect to the stationary portion of the handle. The physician moves the slide 24 to open and close the tissue cutting jaws 18 and obtain a tissue sample.

After a tissue sample has been retrieved, the physician can disengage the bite device and tissue cutting jaws 18 from the distal end 14 of the biopsy forceps 10 and a new bite device member with a new pair of cutting jaws can be secured thereto in order to obtain another tissue sample.

FIG. 2 shows a number of removable bite devices 15 with tissue cutting jaws 18a, 18b, 18c . . . 18o within a tray 30. For each bite device, the jaws project from a proximate base or hub 17. The physician can obtain a tissue sample with each pair of tissue cutting jaws and deposit the jaws with the tissue sample attached back into the tray 30 so that the tray can be forwarded to a pathologist or other analysis center for review and/or diagnosis. Once all the desired tissue samples have been obtained, the biopsy forceps 10 can be either disposed of, or depending upon the materials used to manufacture the biopsy forceps, the handle and sheath portion of the forceps can be sterilized for use with another patient. As will be appreciated, it is not necessary that the tissue samples remain in the tissue cutting jaws after they are obtained. Such samples could be placed in conventional specimen jars.

FIG. 3 illustrates a mechanism for removably securing a bite device with its pair of tissue cutting jaws to the distal end of a biopsy forceps in accordance with one embodiment of the present invention. In this embodiment, the sheath 12 includes an inner elongate member 40 and an outer sleeve 42 that slides over the inner elongate member 40. The distal end of the inner elongate member 40 has a distally extending arm 41 and a transverse distal finger 43 forming a notch 44. The bite device 15 has a proximally extending arm 45 and a transverse proximate finger 47 forming a notch 46 at the proximal end of a pair of tissue cutting jaws 18. In this embodiment, the fingers interlock in the respective notches to join the bite device to the distal end of the inner elongate member 40. The outer sleeve 42 slides over the fingers in order to maintain their interlocked position within the outer sleeve 42. Thus, while the outer sleeve 42 is positioned over the joint between the interlocking fingers, the cutting jaws 18 are secured to the distal end of the biopsy forceps. In one embodiment of the invention, the tissue cutting jaws 18 are biased radially outward such that upon movement of the outer sleeve 42 in the distal direction, the jaws are urged into a closed position. Upon retraction of the outer sleeve 42, the jaws are allowed to open to retrieve a tissue sample. Upon further retraction of the outer sleeve 42, the joint between the interlocking fingers is uncovered and the distal end of the inner elongate member 40 can be removed from the proximal end of the bite member by transverse translation of the two parts.

In the embodiment shown in FIG. 3, the inner elongate member 40 is preferably connected to the stationary handle 22 while the outer sleeve 42 is preferably connected to the movable slide 24 such that the physician can control the opening and closing of the jaws as well as the removal of the bite device with cutting jaws 18 with one hand. A button 26 (shown in FIG. 1) may be provided to limit the movement of the slide 24. The position of the button 26 allows the outer sleeve 42 to be moved past the joint between the interlocking notches in order to exchange the tissue cutting jaws 18.

FIG. 4 shows an alternative embodiment of a mechanism for releasably securing a pair of tissue cutting jaws 18 to the distal end of the biopsy forceps. In this embodiment, the biopsy forceps includes an inner elongate member 60 and an outer sleeve 62. Within the inner elongate member 60 is a spring loaded actuating cable 64 having a structure such as a cylinder 66 disposed at its distal end. The cylinder 66 includes one or more slots 68 in which radially extending pins 70 ride. The one or more slots 68 are transverse to a longitudinal axis of the spring loaded actuating cable 64.

The pins 70 extend radially outwards from the cylinder such that they extend through the side of the inner elongate member 60 and into corresponding holes 72 on a pair of tissue cutting jaws in order to secure the jaws to the forceps. Movement of the cylinder 66 by the cable 64 causes the pins 70 to move radially inwards and outwards. With the pons 70 in the radially outward position, they engage corresponding holes 72 on the proximal end of the tissue cutting jaws 18. When the cable 64 is moved in the proximal direction, the ends of the pins move in the slots 68 to pull the pins 70 radially inwards, thereby releasing the tissue cutting jaws 18 from the forceps so that a new pair of cutting jaws can be installed.

FIG. 5 illustrates yet another mechanism for removably securing a bite member with a pair of tissue cutting jaws 18 to the distal end of the biopsy forceps. In this embodiment, the biopsy forceps has an inner elongate member 80 and an outer sleeve 82. At the distal end of the inner elongate member 80 are one or more spring loaded balls 84 that engage a race or other indentation on the inner surface of the proximal end of the tissue cutting jaws 18. By compression of a ball 18 and its subsequent release within the race or indentation, the tissue cutting jaws 18 are held in a friction fit at the distal end of the biopsy forceps. The outer sleeve 82 is movable over the jaws in order to open and close them as with the embodiments shown in FIGS. 3 and 4. The tissue cutting jaws 18 can simply be pulled off a distal end of the inner elongate member 80 and a new pair of jaws installed by forcing the distal end of the inner elongate member 80 into the proximal end of another set of jaws.

While the preferred embodiment of the invention has been illustrated and described, it will be appreciated that various changes can be made therein without departing from the scope of the invention. Therefore, it is intended that the scope of the invention is to be determined from the following claims and equivalents thereof.

The embodiments of the invention in which an exclusive property or privilege is claimed are defined as follows:

1. A biopsy forceps for obtaining tissue samples, comprising:
    an elongate sheath, the sheath including an inner elongate member and an outer sleeve that are longitudinally movable with respect to one another;
    disposable tissue cutting jaws that are removably secured to a distal end of the inner elongate member; and
    a release mechanism for selectively releasing the tissue cutting jaws from the inner elongate member, including:
        an actuator within the inner elongate member;
        a structure disposed at a distal end of the actuator and defining a slot;
        a pin extending radially from the slot; and
        a hole in a proximal end of the tissue cutting jaws configured to releasably engage with the pin,
    wherein the tissue cutting jaws are configured to remove and retrieve a sample of tissue from a body.

2. The biopsy forceps of claim 1, wherein a hub of a second tissue cutting jaws can be secured to the forceps.

3. The biopsy forceps of claim 1, wherein the tissue cutting jaws are one of a plurality of tissue cutting jaws packaged in a tray; and wherein the tissue cutting jaws and the sample of tissue are stored in the tray.

4. The biopsy forceps of claim 1, wherein each of the tissue cutting jaws has a plurality of teeth.

5. The biopsy forceps of claim 1, wherein movement of the structure by the actuator in a proximal direction causes the pin to disengage from the hole.

6. The biopsy forceps of claim 1, wherein the structure defines a second slot, and the release mechanism further comprises a second pin extending radially from the second slot, and a second hole in the proximal end of the tissue cutting jaws is configured to releasable engage with the second pin.

7. The biopsy forceps of claim 1, wherein the actuator is spring loaded.

8. The biopsy forceps of claim 1, wherein the slot is transverse to a longitudinal axis of the actuator.

9. The biopsy forceps for claim 1, wherein movement of the structure by the actuator in a proximal direction and a distal direction is configured to move the pin radially inwards and outwards respectively.

10. A biopsy forceps for obtaining tissue samples, comprising:
    an elongate sheath, the sheath including an inner elongate member and an outer sleeve that are longitudinally movable with respect to one another;
    disposable tissue cutting jaws that are removably secured to a distal end of the inner elongate member; and
    a release mechanism for selectively releasing the tissue cutting jaws from the inner elongate member, including:
        a spring loaded actuator within the inner elongate member;
        a structure attached to a distal end of the spring loaded actuator and defining a first slot and a second slot, the first slot and the second slot being transverse to a longitudinal axis of the actuator and located on opposing sides of the structure;
        a first pin and a second pin, the first pin extending radially from the first slot, and the second pin extending radially from the second slot;
        a first hole and a second hole in a proximal end of the tissue cutting jaws, the first hole configured to releasably engage with the first pin, and the second hole configured to releasable engage with the second pin,
    wherein the tissue cutting jaws are configured to remove and retrieve a sample of tissue from a body.

11. The biopsy forceps of claim 10, wherein movement of the structure by the spring loaded actuator in a proximal direction and a distal direction is configured to move the first pin and the second pin radially inwards and outwards respectively.

* * * * *

UNITED STATES PATENT AND TRADEMARK OFFICE
CERTIFICATE OF CORRECTION

| | | |
|---|---|---|
| PATENT NO. | : 7,837,631 B2 | Page 1 of 1 |
| APPLICATION NO. | : 10/389851 | |
| DATED | : November 23, 2010 | |
| INVENTOR(S) | : B. H. Diamond et al. | |

It is certified that error appears in the above-identified patent and that said Letters Patent is hereby corrected as shown below:

On the Title page, item (74),
"*Attorney, Agent, or Firm*–Finnegan, Henderson, Farabow, Garrett, & Dunner" should read
--*Attorney, Agent, or Firm*–Finnegan, Henderson, Farabow, Garrett & Dunner--.

Claim 6, col. 4, line 26, "releasable" should read --releasably--.

Claim 9, col. 4, line 32 "The biopsy forceps for claim 1" should read --The biopsy forceps of claim 1--.

Signed and Sealed this
Eighth Day of February, 2011

David J. Kappos
*Director of the United States Patent and Trademark Office*